US00PP19863P2

(12) United States Plant Patent
Pierce

(10) Patent No.: US PP19,863 P2
(45) Date of Patent: Mar. 31, 2009

(54) ***CALIBRACHOA* PLANT NAMED 'CAL SCARE08'**

(50) Latin Name: ***Calibrachoa* sp.**
Varietal Denomination: CAL SCARE08

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/080,149

(22) Filed: Mar. 31, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
(74) *Attorney, Agent, or Firm*—C. A. Whealy

(57) ABSTRACT

A new and distinct cultivar of *Calibrachoa* plant named 'Cal Scare08', characterized by its mounding and outwardly spreading to trailing plant habit; freely branching habit; dense and full plants; early and freely flowering habit; numerous scarlet red-colored flowers; and good garden performance.

1 Drawing Sheet

Botanical designation: *Calibrachoa* sp.
Cultivar denomination: 'CAL SCARE08'.

BACKGROUND OF THE INVENTION

The present invention relates to a new and distinct cultivar of *Calibrachoa*, botanically known as *Calibrachoa* sp. and hereinafter referred to by the name 'Cal Scare08'.

The new *Calibrachoa* is a product of a planned breeding program conducted by the Inventor in Gilroy, Calif. The objective of the breeding program is to create new *Calibrachoa* cultivars with uniform plant habit and numerous attractive flowers.

The new *Calibrachoa* originated from a cross-pollination made by the Inventor in July, 2004 in Gilroy, Calif. of a proprietary selection of *Calibrachoa* sp. identified as code number 57, not patented, as the female, or seed, parent with a proprietary selection of *Calibrachoa* sp. identified as code number 824-1, not patented, as the male, or pollen, parent. The new *Calibrachoa* was discovered and selected by the Inventor as a single flowering plant within the progeny of the stated cross-pollination in a controlled environment in Gilroy, Calif. in September, 2005.

Asexual reproduction of the new *Calibrachoa* by vegetative cuttings in a controlled environment in Gilroy, Calif. since September, 2005 has shown that the unique features of this new *Calibrachoa* are stable and reproduced true to type in successive generations.

SUMMARY OF THE INVENTION

The cultivar Cal Scare08 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cal Scare08'. These characteristics in combination distinguish 'Cal Scare08' as a new and distinct cultivar of *Calibrachoa*:

1. Mounding and outwardly spreading to trailing plant habit.
2. Freely branching habit; dense and full plants.
3. Early and freely flowering habit.
4. Numerous scarlet red-colored flowers.
5. Good garden performance.

The new *Calibrachoa* can be compared to plants of the female parent selection. Plants of the new *Calibrachoa* differ from plants of the female parent selection in the following characteristics:

1. Plants of the new *Calibrachoa* are more vigorous than plants of the female parent selection.
2. Plants of the new *Calibrachoa* have smaller and darker green-colored leaves than plants of the female parent selection.
3. Plants of the new *Calibrachoa* and the female parent selection differ in flower color as plants of the female parent selection have light orange-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are more freely branching than plants of the male parent selection.
2. Plants of the new *Calibrachoa* flower earlier than plants of the male parent selection.
3. Plants of the new *Calibrachoa* and the male parent selection differ in flower color as plants of the male parent selection have deep orange-colored flowers.

Plants of the new *Calibrachoa* can be compared to plants of the cultivar Sunbelre, disclosed in U.S. Plant Pat. No. 14,756. In side-by-side comparisons conducted in Hillscheid, Germany, plants of the new *Calibrachoa* differed from plants of the cultivar Sunbelre in the following characteristics:

1. Plants of the new *Calibrachoa* were more compact and prostrate than plants of the cultivar Sunbelre.
2. Plants of the new *Calibrachoa* were more freely branching than plants of the cultivar Sunbelre.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph comprises a side perspective view of a typical flowering plant of 'Cal Scare08'.

DETAILED BOTANICAL DESCRIPTION

The aforementioned photograph and following observations, measurements and values describe plants grown in Hillscheid, Germany under commercial practice during the summer in an outdoor nursery. Plants used for the photograph were grown in 15-cm containers for about 16 weeks. Plants used for the description were grown in 25-cm hanging basket containers for about seven months. In the following description, color references are made to The Royal Horticultural Society Colour Chart, 2001 Edition, except where general terms of ordinary dictionary significance are used.

Botanical classification: *Calibrachoa* sp. cultivar Cal Scare08.

Parentage:

*Female, or seed, parent.*—Proprietary selection of *Calibrachoa* sp. identified as code number 57, not patented.

*Male, or pollen, parent.*—Proprietary selection of *Calibrachoa* sp. identified as code number 824-1, not patented.

Propagation:

*Type.*—By vegetative cuttings.

*Time to initiate and develop roots.*—About 18 to 23 days.

*Root description.*—Fibrous; color, close to 155D.

Plant description:

*Plant and growth habit.*—Mounding and outwardly spreading to trailing plant habit. Freely branching habit with about 30 to 35 primary lateral branches each with about four to six secondary lateral branches; full and dense plants. Vigorous growth habit.

*Plant height.*—About 30 cm to 35 cm.

*Plant diameter.*—About 75 cm.

Lateral branch description:

*Length.*—About 40 cm to 45 cm.

*Diameter.*—About 3 mm to 4 mm.

*Internode length.*—About 2.5 cm to 3.5 cm.

*Strength.*—Strong; flexible.

*Aspect.*—Initially upright to outwardly spreading to trailing.

*Texture.*—Densely hirsute.

*Color.*—Close to either 143C or 145A; towards the apex, close to 177A or 148A.

Foliage description:

*Arrangement.*—Alternate, simple.

*Length.*—About 3.4 cm to 4 cm.

*Width.*—About 1.7 cm to 1.8 cm.

*Shape.*—Elliptic.

*Apex.*—Obtuse.

*Base.*—Attenuate to acute.

*Margin.*—Entire.

*Texture, upper surface.*—Hirsute.

*Texture, lower surface.*—Hirsute; more dense at the margins and midrib.

*Venation pattern.*—Pinnate; arcuate.

*Color.*—Developing foliage, upper surface: Close to 137D. Developing foliage, lower surface: Close to 138A. Fully expanded foliage, upper surface: Close to 137B to 137C; venation, similar to lamina. Fully expanded foliage, lower surface: Close to 137D; venation, close to 144B.

*Petioles.*—Length: About 3 mm to 4 mm. Diameter: About 2 mm to 3 mm. Texture, upper and lower surfaces: Hirsute; more dense at the margins and midrib. Color, upper and lower surfaces: Close to 143C to 143D.

Flower description:

*Flower arrangement and habit.*—Single salverform flowers arranged singly arising from upper leaf axils. Freely flowering habit with usually about 50 flowers developing per plant. Flowers not persistent. Flowers face mostly outwardly.

*Fragrance.*—None detected.

*Natural flowering season.*—Plants of the new *Calibrachoa* initiate and develop flowers about eight weeks after planting. Plants flower continuously during the summer in Hillscheid, Germany.

*Flower longevity.*—Individual flowers last about five to eight days on the plant.

*Flower diameter.*—About 3 cm to 3.2 cm.

*Flower length (height).*—About 2.6 cm to 3 cm.

*Corolla tube length.*—About 1.4 cm to 1.6 cm.

*Flower bud.*—Shape: Oblong, tubular. Length: About 2.4 cm. Diameter: About 7 mm to 9 mm. Color: Close to 160A; random blotches, close to 51C.

*Corolla.*—Arrangement: Five petals fused at the base and opening into a flared trumpet; flowers star-shaped. Petal shape: Roughly obovate. Petal apex: Truncate to slightly retuse. Petal margin: Entire; weakly undulate. Petal texture, upper and lower surfaces: Papillose, satiny; along the veins, hirsute. Color: Petal, when opening, upper surface: Close to 46B. Petal, when opening, lower surface: Close to 52B. Petal, fully opened, upper surface: Close to 44A to 44B; venation, close to 44B. With development, color of some flowers becoming closer to 54B. Petal, fully opened, lower surface: Close to 51C; towards the margins, close to 51B. Throat: Close to 7A. Tube: Close to 12C to 12D.

*Calyx.*—Arrangement: One star-shaped calyx tube with five sepals fused at the base per flower. Sepal length: About 1.2 cm to 1.4 cm. Sepal width: About 3 mm to 4 mm. Sepal shape: Lanceolate. Sepal apex: Acute to obtuse. Sepal margin: Entire. Sepal texture, upper and lower surfaces: Densely hirsute. Color, upper surface: Close to 137C to 137D. Color, lower surface: Close to 137D.

*Peduncles.*—Length: About 2 cm to 2.8 cm. Diameter: About 1 mm. Strength: Moderately strong; flexible. Texture: Hirsute. Color: Close to 143C; towards the flower, close to 146A.

*Reproductive organs.*—Stamens: Quantity/arrangement: About five per flower. Filament length: About 8 mm to 11 mm. Filament diameter: About 1 mm. Filament color: Close to 4D. Anther shape: Reniform, two-parted. Pollen amount: Moderate. Pollen color: Close to 8A. Pistils: Quantity: One per flower. Pistil length: About 9 mm to 10 mm. Style color: Close to 145D. Stigma shape: Ovate. Stigma color: Close to 145A. Ovary color: Close to 145D.

*Seeds/fruits.*—Seed and fruit development have not been observed.

Garden performance: Plants of the new *Calibrachoa* have been observed to have good garden performance and tolerate wind, rain and temperatures ranging from about 5° C. to about 30° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Cal Scare08' as illustrated and described.

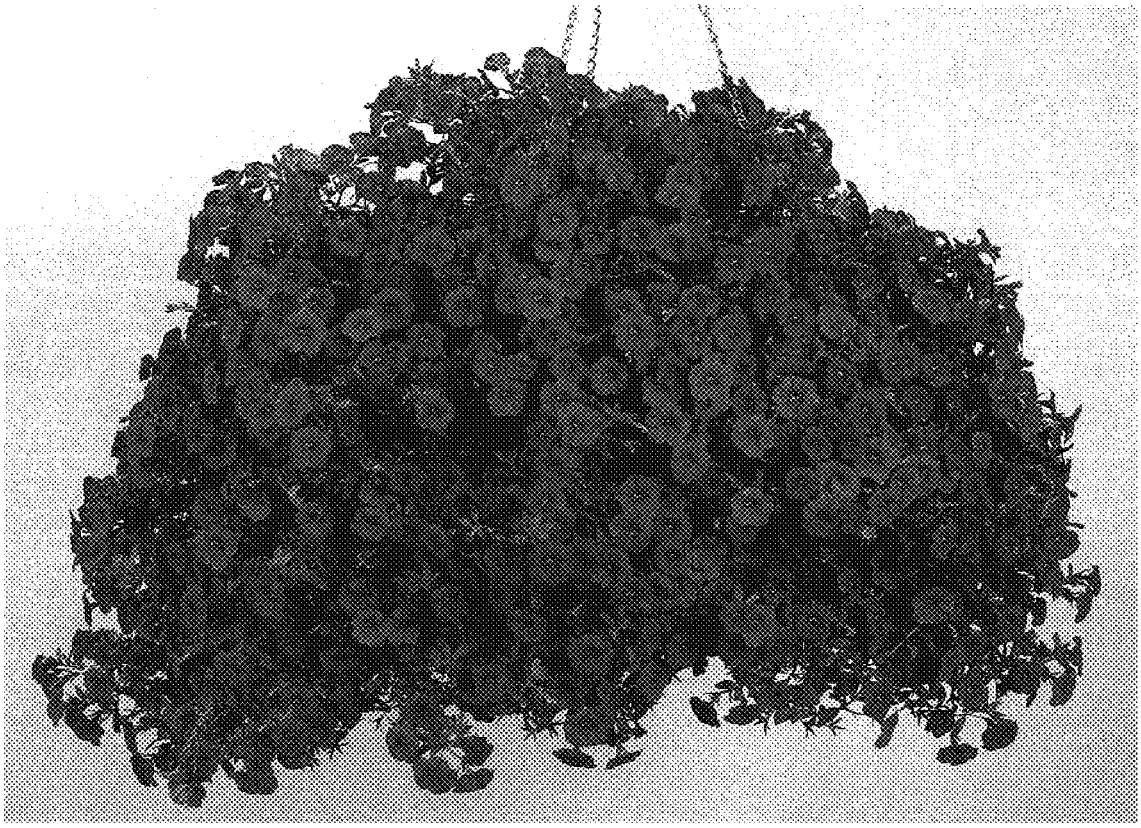

* * * * *